(12) United States Patent
Chevallet

(10) Patent No.: US 6,649,046 B2
(45) Date of Patent: Nov. 18, 2003

(54) DEVICE FOR MEASURING NEGATIVE PRESSURES IN AN EXTRACORPOREAL BLOOD CIRCUIT

(75) Inventor: Jacques Chevallet, Serezin du Rhone (FR)

(73) Assignee: Hospal International Marketing Management, Lyons (FR)

( * ) Notice: Subject to any disclaimer, the term of this patent is extended or adjusted under 35 U.S.C. 154(b) by 137 days.

(21) Appl. No.: 10/004,858

(22) Filed: Dec. 7, 2001

(65) Prior Publication Data

US 2002/0104786 A1 Aug. 8, 2002

(30) Foreign Application Priority Data

Dec. 8, 2000  (FR) .............................................. 00 15970

(51) Int. Cl.[7] .......................... B01D 65/00; G01L 7/08; G01L 13/02
(52) U.S. Cl. ............................ 210/90; 210/97; 73/715; 73/716; 73/717; 73/723
(58) Field of Search .............................. 210/86, 90, 97; 73/715, 716, 717, 723, 1.57, 1.68, 49.1

(56) References Cited

U.S. PATENT DOCUMENTS 6,129,656 A    10/2000   Blakeslee et al. ............. 494/45

FOREIGN PATENT DOCUMENTS

| EP | 0 685 721   | 12/1995 |
| WO | WO 99/13926 | 3/1999  |

*Primary Examiner*—John Kim
(74) *Attorney, Agent, or Firm*—Young & Thompson

(57) ABSTRACT

A device for measuring the pressure of blood in a pipe (44) of an extracoporeal blood cicuit, includes a pressure measurement section (46) having a compartment (58) which is delimited especially by a main wall (64) and by a secondary wall (65) facing it. The two walls (64, 65) have a hole (66, 84) which is closed by a closure element (68, 86) which can be elastically deformed under the effect of the blood pressure, and the compartment (58) has a spacer (94) which transmits the movements from the closure element (86) of the secondary wall (65) to the closure element (68) of the main wall (64), so that a load sensor (56) can measure a force which corresponds to a so-called "negative" blood pressure.

13 Claims, 3 Drawing Sheets

DEVICE FOR MEASURING NEGATIVE PRESSURES IN AN EXTRACORPOREAL BLOOD CIRCUIT

FILED OF THE INVENTION

The present invention relates to a device for measuring blood pressure.

More particularly, the present invention relates to a device for measuring the pressure of blood which is used in an extracorporeal blood treatment device in which the blood is taken from a patient in order to be treated then reintroduced into the body of the patient (especially for the purpose of carrying out dialysis) by means of an extracorporeal blood circuit comprising pipes and including at least one section for measuring the pressure of blood circulating in a pipe.

BACKGROUND OF THE INVENTION

A known type of pressure measurement section forms a compartment which is delimited especially by a main wall and by a secondary wall facing it, the two walls being substantially rigid and parallel; the main wall comprises a hole which is sealed by a main closure element, the internal face of which is in contact with the blood and the external face of which is in contact with the ambient air, it being possible to elastically deform or displace the entire main closure element along a deformation or displacement axis which is substantially orthogonal to its general plane, under the effect of the blood pressure; a portion of the external face of the main closure element, in its rest state, is in direct or indirect contact with a load sensor which is able to measure the force applied axially to the internal face of the main closure element by the pressure of the blood, in order to calculate therefrom the value of this pressure.

Generally, this type of extracorporeal blood treatment device comprises a circuit part which is formed from a casing, or cassette, of the "disposable" type, integrating pipes which are connected to the extracorporeal blood circuit.

The pressure measurement section may be an attached module which is mounted in a housing associated with the casing.

The casing is mounted on a support apparatus which comprises, for example, sensors, display means, pumping means, a control interface, an electronic control unit, etc.

In this type of extracorporeal blood treatment device, the blood pressure must be measured without contact between the measuring member and the blood.

Several systems for carrying out this pressure measurement are known.

In a first pressure measurement system, which is shown in FIG. 1, a pressure measurement section 10 in a pipe 12 comprises a measurement chamber 14 in which a membrane 16, or diaphragm, separates the blood flowing in the pipe 12 from the air contained in a compartment 18.

The membrane 16 can be deformed along a deformation axis A—A orthogonal to its general plane, such that it is axially displaced according to the blood pressure in the pipe 12.

The extreme deformation positions of the membrane 16 are shown in dotted lines.

The air compartment 18 is sealed shut when the pressure measurement section 10 is mounted on a support apparatus 20.

The support apparatus 20 comprises a sensor 22 which directly measures the pressure in the air compartment 18.

When the blood pressure changes, the membrane 16 is axially displaced to an equilibrium position in which the pressure is equal on each side of the membrane 16.

The pressure measured by the sensor 22 in the air compartment 18 is therefore equal to the blood pressure in the pipe 12.

By virtue of a suitable geometry, in particular by virtue of a suitable volume of the compartment 18 and a suitable surface for the membrane 16, this first pressure measurement system makes it possible to measure, on the one hand, so-called "positive" blood pressures, that is blood pressures which are greater than a reference pressure, in this case atmospheric pressure, and, on the other hand, so-called "negative" blood pressures, that is blood pressures which are less than the reference pressure.

This measurement system operates correctly provided there are no leaks in the air compartment 18, otherwise the membrane 16 is then displaced to its end stop and it no longer carries out the function of transmitting pressure.

The sealing of the air compartment 18 during mounting of the pressure measurement section 10 on the support apparatus 20 is a weak point of the measurement system.

In particular, the seal may be impaired while the measurement system is in use.

In a second pressure measurement system, which is shown in FIG. 2, the pressure measurement section 10 forms a compartment 24 containing the blood and a wall 26 of which includes a hole 28 which is sealed by a flexible membrane 30.

When the pressure measurement section 10 is mounted on the support apparatus 20, the external face of the central part of the flexible membrane 30 is in contact with a load transmitter 32 which is inserted between the membrane 30 and a load sensor 34.

The load sensor 34 makes it possible to measure the forces applied to the internal face of the membrane 30 due to the effect of the blood pressure in the compartment 24, when the blood pressure is greater than the ambient air pressure.

The blood pressure is calculated from the equation:

$$P = \frac{F - F_0}{S_a} \quad (1)$$

In this equation, F is the force measured by the load sensor 34, $F_0$ is the force measured in the rest state, that is in the absence of a pressure gradient between the two sides (external and internal faces) of the membrane 30, and $S_a$ is the area of the active surface of the membrane 30.

The area of the active surface $S_a$ of the membrane 30 has a value between the total area of the internal face of the membrane 30 in contact with the blood and the area of contact between the membrane 30 and the load transmitter 32.

For very flexible membranes 30, the active surface $S_a$ is substantially equivalent to the area of contact between the membrane 30 and the load transmitter 32.

This measurement system makes it possible to measure a positive pressure but it does not allow a negative pressure to be measured.

This is because, for negative pressures, the membrane 30 tends to come away from the load transmitter 32. The load sensor 34 can therefore no longer measure the forces which are applied to the membrane 30.

This system has therefore been adapted to measure negative pressures.

In order that the load sensor 34 can continue to measure the forces which are applied to the membrane 30, when the blood pressure is negative, the membrane 30 is secured in axial displacement to the load transmitter 32.

Thus, according to an improved embodiment of the second pressure measurement system, which is shown in FIG. 3, the membrane includes a metal disc 36 on its external face and the load transmitter 32 includes a magnet 38 at its axial end facing the membrane 30.

The magnetic attraction exerted by the magnet 38 on the metal disc 36 makes it possible to secure the membrane 30 in axial displacement to the load transmitter 32.

When the pressure is positive, the membrane 30 exerts an axial force which pushes against the load transmitter 32.

When the pressure is negative, the membrane 30 exerts an axial force which pulls on the load transmitter 32.

This device for securing the membrane 30 to the load transmitter 32 is expensive since it requires a special membrane 30 fitted with a metal disc 36 and a special load transmitter 32 fitted with a magnet 38.

The metal disc 36 must have a large area in order to allow effective magnetic coupling.

Furthermore, the membrane 30 experiences a significant jolt when the metal disc 36 "sticks" to the magnet 38 of the load transmitter 32, which could impair its mechanical characteristics.

The invention aims to remedy these drawbacks.

SUMMARY OF THE INVENTION

For this purpose, the invention proposes a device for measuring the pressure of blood in a pipe of an extracorporeal blood circuit, comprising a pressure measurement section having a compartment which is delimited especially by a main wall and by a secondary wall facing it, the two walls being substantially rigid and parallel, the main wall having a hole which is sealed by a main closure element, the internal face of which is in contact with the blood and the external face of which is in contact with the ambient air, it being possible to elastically deform or displace the entire main closure element along a deformation or displacement axis, which is substantially orthogonal to its general plane, under the effect of the blood pressure, the main closure element being designed to engage with a load sensor so that a portion of the external face of the main closure element, in its rest state, is in direct or indirect contact with the load sensor which can measure the force applied axially to the internal face of the main closure element by the blood pressure, in order to calculate therefrom the value of this pressure, characterized in that the pressure measurement section comprises:

in its secondary wall, facing the hole of the main wall, a secondary hole which is sealed by a secondary closure element similar to the main closure element, the deformation or displacement axis of which is substantially coincident with that of the main closure element, the area of the internal face of the secondary closure element being greater than the area of the internal face of the main closure element, such that when the pressure of the blood is less than the pressure of the ambient air, the axial displacement of the secondary closure element towards the main closure element is greater than the axial displacement of the main closure element towards the secondary closure element;

and comprising, in the compartment, a transmission spacer which, when the pressure of the blood and the pressure of the ambient air are substantially equal, occupies a rest position in which it is in contact by a first axial end with the internal face of the main closure element and, by a second axial end, with the internal face of the secondary closure element;

such that when the blood pressure is less than the ambient air pressure, the spacer transmits the axial displacement, in the direction of the load sensor, from the secondary closure element to the main closure element, so that the load sensor can measure the resultant axial force in order to calculate therefrom the value of the blood pressure.

According to other characteristics of the invention:

the pressure measurement section comprises axial displacement guiding means for the transmission spacer;

the spacer has an axial rod provided, at least at one of its axial ends, with an axial support plate, the external face of which is adjacent and substantially parallel to the internal face of the associated closure element, when the spacer occupies its rest position;

the rod comprises a support plate at each one of its axial ends;

the area of the external face of each support plate is substantially equal to the area of the internal face of the associated closure element;

each of the closure elements and each of the support plates has substantially the shape of a disc;

the internal face of the main wall and the internal face of the secondary wall each comprise a rim, around the associated closure element, which extends axially towards the inside and which delimits a section of guide tube of a diameter substantially equal to the diameter of the associated support plate, for the purpose of axially guiding the transmission spacer;

the transmission spacer is attached to one of the closure elements;

at least one closure element is made in a single piece with the associated rigid wall, and the transmission spacer is made in a single piece with one closure element which is made in a single piece with the associated rigid wall;

the transmission spacer is made by moulding with a closure element which is itself made by moulding with the associated rigid wall;

the transmission spacer is secured in axial displacement to the secondary closure element;

the area of the secondary closure element is substantially twice the area of the main closure element;

the pressure measurement section comprises a sensor which identifies the direction of the axial displacement of the secondary closure element, so as to determine whether the axial force measured by the load sensor corresponds to a measurement of blood pressure which is above or below the pressure of the ambient air.

BRIEF DESCRIPTION OF THE DRAWINGS

Other characteristics and advantages of the invention will appear on reading the following detailed description, for the understanding of which reference may be made to the appended drawings in which:

In the following description, identical or similar elements will be denoted by identical references.

FIG. 4 shows an extracorporeal blood treatment device 40 for the purpose of carrying out dialysis.

DETAILED DESCRIPTION OF THE INVENTION

Figure 1:
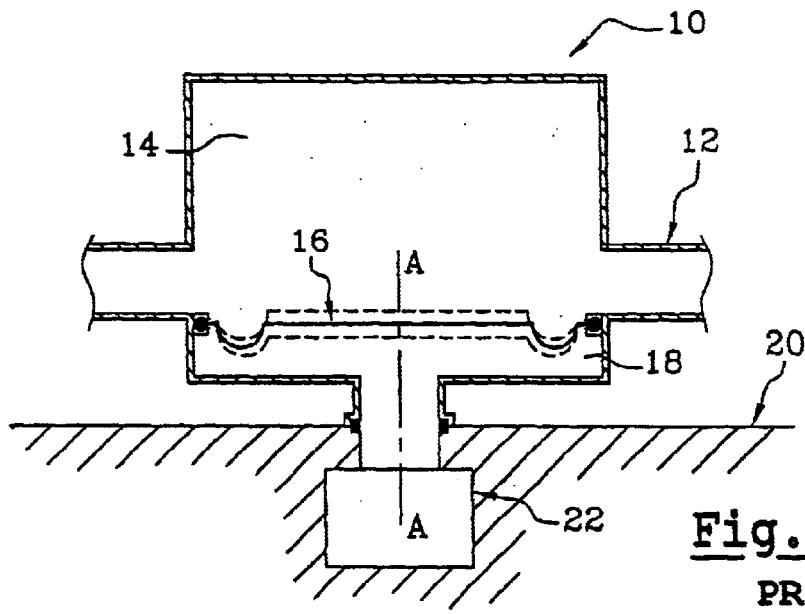
FIG. 1 is a cross-sectional schematic view showing a first type of pressure measurement system according to the prior art.
Figure 2:
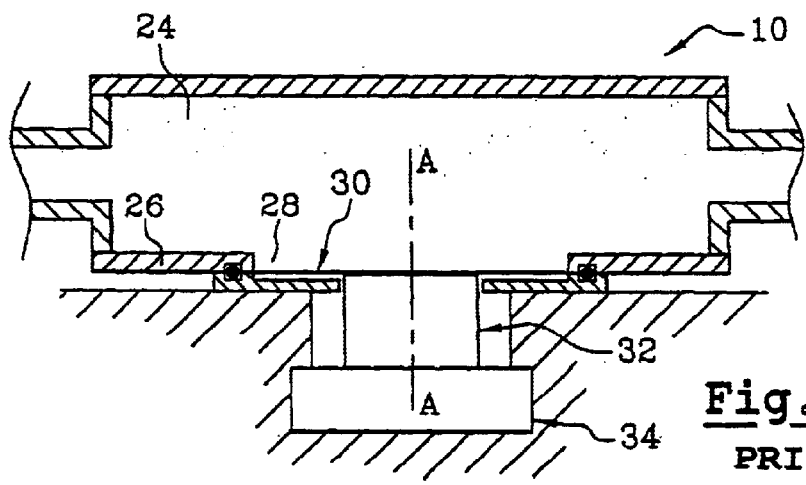
FIG. 2 is a view, similar to that of FIG. 1, which shows a second type of pressure measurement system according to the prior art.
Figure 3:
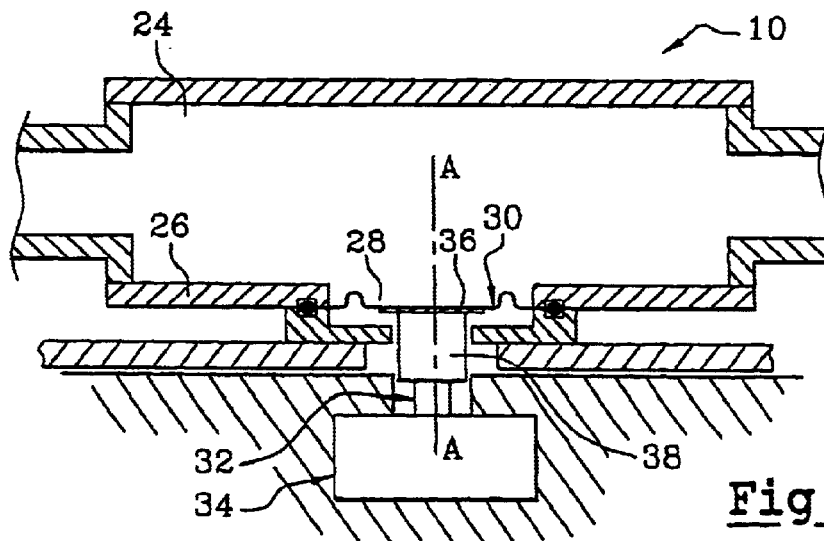
FIG. 3 is a view, similar to that of FIG. 1, which shows an improvement to the pressure measurement system of FIG. 2 according to the prior art.
Figure 4:
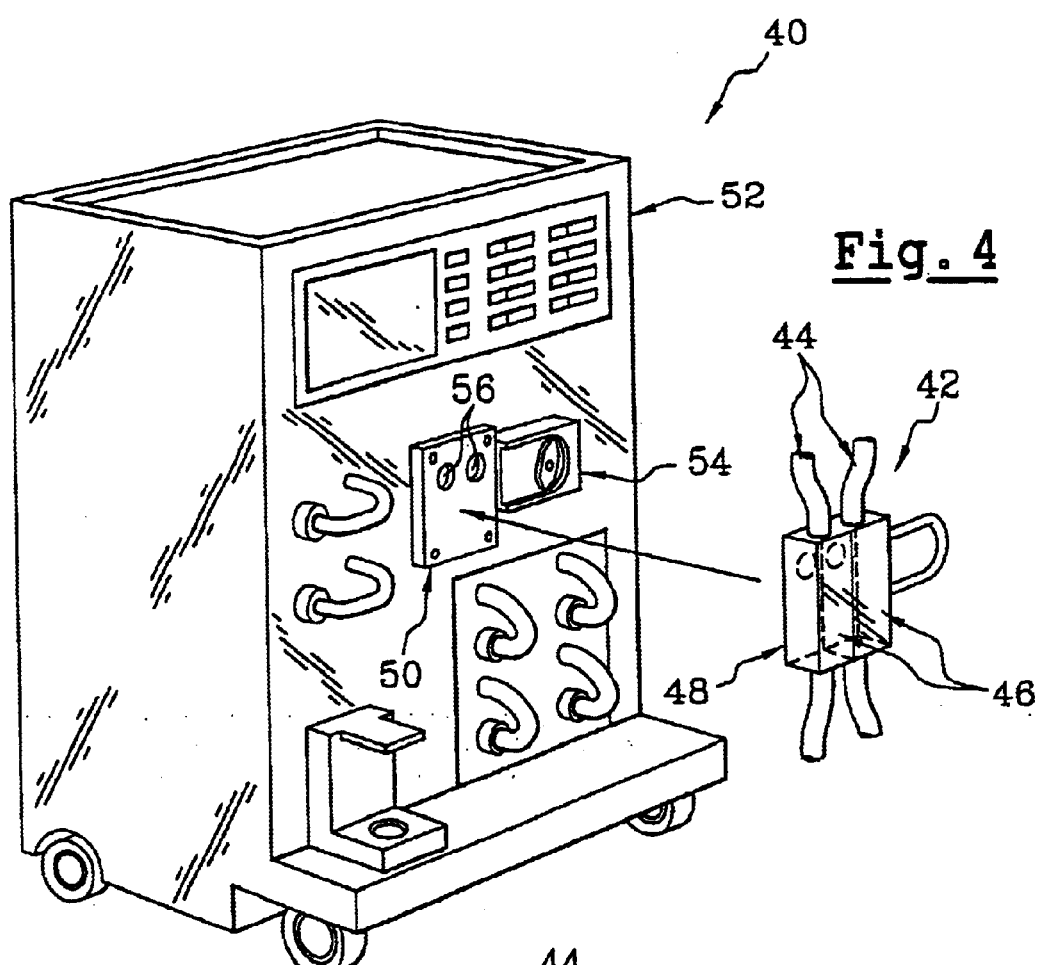
FIG. 4 is a perspective view which shows schematically an extracorporeal blood treatment device made according to the teachings of the invention.

This device 40 is designed to take blood from a patient, to treat it for the purpose of carrying out dialysis, then to reintroduce it into the body of the patient.

This device 40 comprises an extracorporeal blood circuit 42 (here shown only in part) having pipes 44 and comprising at least one section 46 for measuring the pressure of blood flowing in a pipe 44.

In this case, part of the extracorporeal blood circuit 42 is formed by a substantially parallelepipedal casing 48, also called cassette, which contains in its thickness pipes 44 for the blood flow, which are connected to other pipes 44 of the extracorporeal blood circuit 42.

In this case, the cassette 48 comprises two similar pressure measurement sections 46 which are contained therein.

The cassette 48 is designed to be mounted on a support plate 50 of a dialysis apparatus 52 which comprises, in particular, pumping means 54 to make the blood flow in the circuit 42 and means for controlling certain parameters of the circuit 42, in particular load sensors 56 which engage with the sections 46 in order to control the pressure in the pipes 44 of the circuit 42.

The cassette 48 is made, for example by moulding, of polycarbonate or polypropylene or of another suitable material.

In the rest of the description, only a single section 46 will be described.

Figure 6:
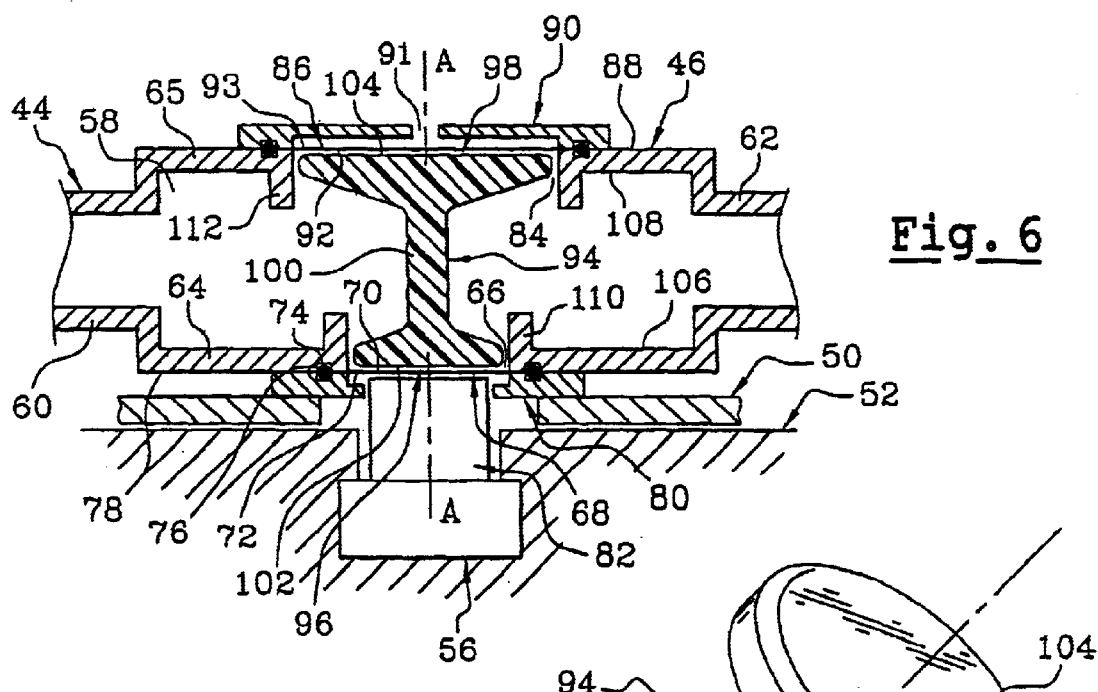
FIG. 6 is a view, similar to that of FIG. 1, which shows a pressure measurement section of the device of FIG. 4, according to the teachings of the invention.

The pressure measurement section 46, which is shown schematically in FIG. 6, in this case forms a substantially parallelepipedal compartment 58 which is inserted between two branches 60, 62 of a pipe 44, and which is for example moulded with the cassette 48.

According to an alternative embodiment (not shown) of the pressure measurement section 46, the latter may be a module attached to the cassette 48.

The compartment 58 is delimited especially by a main wall 64 and a secondary wall 65 which are substantially rigid and parallel.

The main wall 64 includes a hole 66 which is sealed by a main closure element 68, the internal face 70 of which is in contact with the blood and the external face 72 of which is in contact with the ambient air.

In the rest of the description, an axial orientation will be defined as following an axis A—A which is substantially orthogonal to the general plane of the main wall 64 and which passes through the centre of the hole 66.

When the cassette 48 is mounted on its support plate 50, the main wall 64 of the pressure measurement section 46 is designed to be placed facing the support plate 50, so that the main closure element 68 is facing a load sensor 56.

Figure 5:
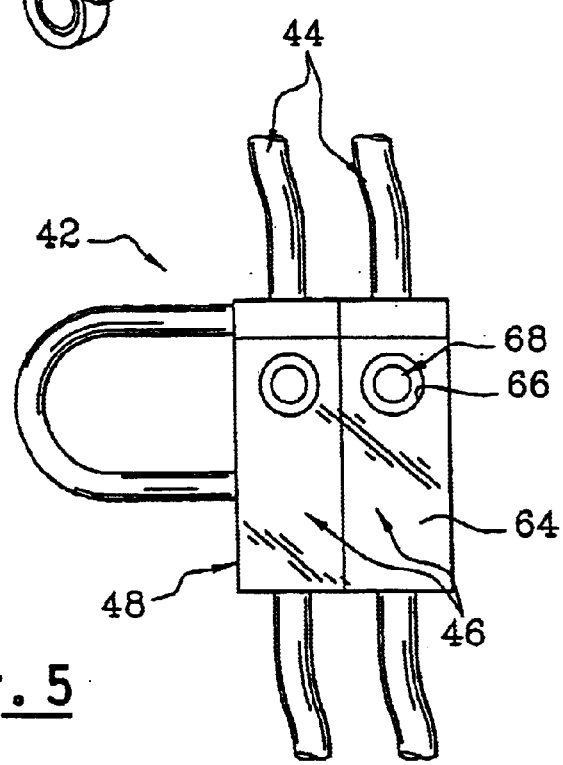
FIG. 5 is a top view which shows schematically the cassette of the device of FIG. 4.

FIG. 5 shows the cassette 48 seen from the side of the main wall 64.

In this case, the main closure element 68 is a flexible membrane which is substantially disc-shaped.

In FIG. 6, the main membrane 68 has a peripheral torus-shaped beading 74 for its assembly in a complementary annular groove 76 which is made in the external face 78 of the main wall 64, in the vicinity of the hole 66.

A retaining ring 80 is fixed, for example by adhesive bonding, to the external face 78 of the main wall 64, over the torus-shaped beading 74, so as to axially retain the main membrane 68.

It is possible to deform the entire main membrane 68 along a deformation axis A—A which is substantially orthogonal to its general plane, under the effect of the blood pressure.

When the main membrane 68 is in its rest state, that is, when it is not deformed, since the blood pressure is substantially equal to the ambient air pressure, the central part of its external face 72 is in contact with a load transmitter 82, itself attached to a load sensor 56.

The load sensor 56 measures the force applied axially to the internal face 70 of the main membrane 68 by the blood pressure, in order to calculate therefrom the value of the said pressure.

Advantageously, the load sensor 56 is of the strain gauge type.

Note that when the system is in the rest state, the main membrane 68 is lightly tensioned, that is elastically deformed, by the force transmitter 82, by an initial axial pressing force $F_0$, so as to guarantee contact between the main membrane 68 and the force transmitter 82.

In accordance with the teachings of the invention, the compartment 58 comprises, in its secondary wall 65, facing the hole 66 of the main wall 64, a secondary hole 84 which is sealed by a secondary closure element 86 similar to the main closure element 68, in this case by a secondary flexible membrane.

The secondary membrane 86 is attached to the external face 88 of the secondary wall 65 in a manner similar to the main membrane 68, by a secondary retaining ring 90.

Advantageously, the secondary ring 90 is almost closed, which makes it possible to protect the secondary membrane 86, and it therefore includes a central orifice 91 of small diameter.

The central orifice 91 makes it possible to put the external face 93 of the secondary membrane 86 in contact with the ambient air.

The deformation axis A—A of the secondary membrane 86 is substantially coincident with that of the main membrane 68.

The area of the internal face 92 of the secondary membrane 86 is greater than the area of the internal face 70 of the main membrane 68 such that, when the blood pressure is less than the ambient air pressure, the axial deformation of the secondary membrane 86 in the direction of the main membrane 68 is greater than the axial deformation of the main membrane 68 in the direction of the secondary membrane 86.

The compartment 58 also comprises a transmission spacer 94 which is inserted axially between the two membranes 68, 86.

When the blood pressure and the ambient air pressure are substantially equal, the spacer 94 occupies a rest position in which it is in contact, by a main axial end 96, with the internal face 70 of the main membrane 68 and, by a secondary axial end 98, with the internal face 92 of the secondary membrane 86.

Figure 7:
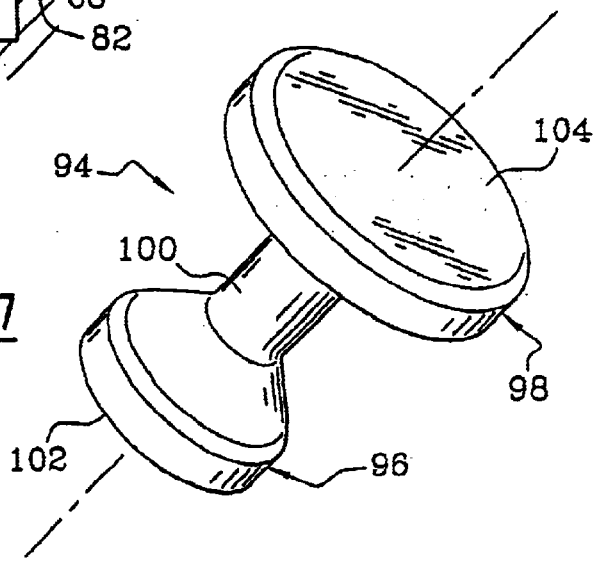
FIG. 7 is a schematic perspective view which shows the transmission spacer of the pressure measurement section of FIG. 6.

In this case, the spacer 94 has the overall shape of a "bobbin", as shown in FIG. 7.

It comprises an axial rod 100 which is fitted, at each of its axial ends, with an axial support plate 96, 98, or end plate, the external face 102, 104 of which is adjacent and substantially parallel to the internal face 70, 92 of the associated membrane 68, 86, when the spacer 94 is in its rest position.

Each support plate 96, 98 in this case has the overall shape of a disc, the diameter of which is substantially equal to the diameter of the internal face 70, 92 of the associated membrane 68, 86.

Advantageously, the internal face 106 of the main wall 64 and the internal face 108 of the secondary wall 65 each have a rim 110, 112, around the associated hole 66, 84, which extends axially towards the inside and which delimits a guide tube section with a diameter substantially equal to the diameter of the associated support plate 96, 98 of the spacer 94, for the purpose of axially guiding the transmission spacer 94.

The axial guiding of the spacer 94 makes it possible to prevent it being offset transversely, or about a rotation axis which is substantially transverse with respect to the deformation axis A—A of the membranes 68, 86.

Note that the spacer 94 is made, preferably by moulding of a light material, for example of polycarbonate or polypropylene.

When the blood pressure in the compartment 58 is greater than the ambient air pressure, that is when the pressure is called "positive", the spacer 94 does not affect the operation of the membranes 68, 86 since the two membranes 68, 86 are deformed axially towards the outside, moving away from the spacer 94, the main membrane 68 applying a main axial pressing force $F_p$ against the force transmitter 82.

The absolute value of the main force $F_p$ can thus be expressed as follows:

$$F_p = F_0 + p \cdot S_p \quad (2)$$

In this equation (2), $F_0$ is the initial axial pressing force measured by the load sensor in the rest state of the pressure measurement system, p is the difference between the blood pressure and the ambient air pressure which are applied to the membranes 68, 86, and $S_p$ is the area of the active surface of the main membrane 68.

When the blood pressure in the compartment 58 is less than the ambient air pressure, that is when the pressure is called "negative", the two membranes 68, 86 tend to be deformed axially towards the inside of the compartment 58.

The main membrane 68 then exerts a main axial pressing force $F_p$ on the external face 102 of the main plate 96 directed towards the secondary membrane 86, and the secondary membrane 86 then exerts a secondary axial pressing force $F_S$ on the external face 104 of the secondary plate 98 directed towards the main membrane 68.

The two forces $F_p$, $F_S$ are therefore in opposite directions.

The absolute value of the main force $F_p$ can be expressed as follows:

$$F_p = p \cdot S_p \quad (3)$$

In this equation (3), p is the difference between the blood pressure and the ambient air pressure which are applied to the membranes 68, 86, and $S_p$ is the area of the active surface of the main membrane 68.

The absolute value of the secondary force $F_s$ can be expressed in a manner similar to equation (3), as follows:

$$F_s = p \cdot S_s \quad (4)$$

In this equation (4), $S_s$ is the area of the active surface of the secondary membrane 86.

By design, the area $S_s$ of the active surface of the secondary membrane 86 is greater than the area $S_p$ of the active surface of the main membrane 68.

The secondary force $F_s$ is therefore greater than the main force $F_p$.

Advantageously, a secondary active surface $S_s$ is chosen, the area of which is equal to twice that of the main active surface $S_p$.

The absolute value of the secondary force $F_s$ can then be expressed as follows:

$$F_s = 2p \cdot S_p \quad (5)$$

The absolute value of the resultant axial force $F_r$, which is applied to the load transmitter 82 and which is directed from the main membrane 68 to the load sensor 56, is then expressed as follows:

$$F_r = F_0 + F_s - F_p = F_0 + p \cdot S_p \quad (6)$$

In this equation, $F_0$ is the initial axial pressing force, or pretensioning force, which is measured by the load sensor in the rest state of the pressure measurement system.

Consequently, for the same pressure difference p, the resultant force $F_r$ of equation (6) and the main force $F_p$ of equation (2) are equal.

For the same pressure difference p, whatever the direction of the pressure variation, the load sensor 56 will measure an identical value of force $F_r$ and it will therefore calculate therefrom a same value of blood pressure.

Note that the spacer 94 makes it possible to transmit the resultant force $F_r$ to the main membrane 68 and therefore to the load transmitter 82.

Note also that the load sensor 56 is not capable of determining whether the axial pressing force that it measures corresponds to a positive or negative blood pressure.

According to an alternative embodiment (not shown) of the invention, an additional sensor is placed in the vicinity of the central part of the external wall 93 of the secondary membrane 86, so as to detect, for example, a possible axial deformation of the secondary membrane 86 towards the outside.

If the additional sensor detects such an axial deformation, it can then be deduced that the force measured by the load sensor 56 corresponds to a positive pressure, otherwise it can be deduced that the force measured by the load sensor 56 corresponds to a negative pressure.

It is found that the greater the difference between the area of the internal face 70 of the main membrane 68 and the area of the internal face 92 of the secondary membrane 86, the more the sensitivity and efficiency of the negative pressure measurement increases.

However, the area of the internal face 70 of the main membrane 68 should not be too small otherwise the mechanical ability for axial deformation of the main membrane 68 is decreased and the sensitivity of the main membrane 86 to the resultant force $F_r$ transmitted by the spacer 94, is decreased.

According to an alternative embodiment (not shown) of the invention, one of the support plates 96, 98 of the transmission spacer 94 is attached by known means to the associated membrane 68, 86, for example by adhesive bonding.

Note that the transmission spacer 94 should not be attached to the two membranes 68, 86, otherwise, in the case of positive pressure, the secondary membrane 86 would cause the main membrane 68 to be axially displaced towards the outside, on the side opposite the load transmitter 82, which would distort the measurements carried out by the load sensor 56.

Figure 8:
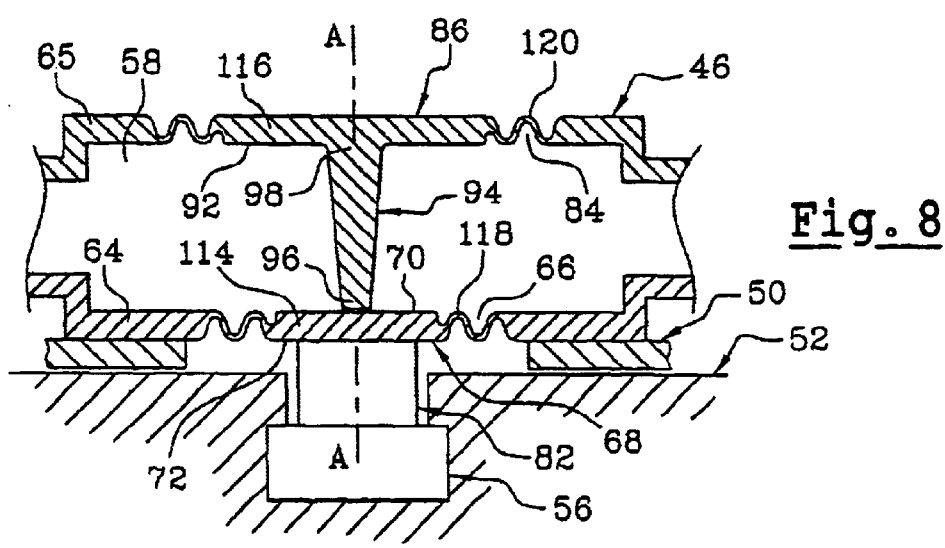
FIG. 8 is a view, similar to that of FIG. 1, which shows a variant of the pressure measurement section of FIG. 6 comprising closure elements moulded in their associated rigid walls.

FIG. 8 shows an alternative embodiment of the invention in which the closure elements 68, 86 of the holes 66, 84 of the main wall 64 and the secondary wall 65, respectively, are each made in a single piece with the associated wall 64, 65.

In this case, each closure element 68, 86 comprises a disc-shaped substantially rigid central pellet 114, 116, which is delimited by a thinned peripheral annular region 118, 120 with an axial thickness less than the axial thickness of the associated rigid wall 64, 65, so as to form an elastically deformable region.

Thus, under the effect of the blood pressure in the compartment 58, and by virtue of the elastic deformation of its thinned region 118, 120, it is possible for each central pellet 114, 116 to be displaced overall along a displacement axis which is substantially orthogonal to the general plane of the pellet 114, 116 and which corresponds to the deformation axis A—A of the membranes 68, 86 of the embodiment shown in FIG. 6.

In its rest state, the external face 72 of the central pellet 114 of the main closure element 68, or main pellet 114, is in contact with the load transmitter 82.

Advantageously, the transmission spacer 94 is made in a single piece, in this case by moulding, with the central pellet 116 of the secondary closure element 86, or secondary pellet 116.

In the embodiment which is shown here, the transmission spacer 94 has the shape of a frustoconical finger, the base 98 of which is moulded on the internal face 92 of the secondary pellet 116 and the free axial end 96 of which bears axially against the internal face 70 of the main pellet 114, when the system is in its rest state.

Of course, it is possible to combine the different characteristics which have been described above, without departing from the field of the present invention.

What is claimed is:
1. Device for measuring the pressure of blood in a pipe (44) of an extracorporeal blood circuit (42), comprising a pressure measurement section (46) having a compartment (58) which is delimited especially by a main wall (64) and by a secondary wall (65) facing the main wall (64), the two walls (64, 65) being substantially rigid and parallel, the main wall (64) having a hole (66) which is sealed by a main closure element (68) having an internal face (70) which is in contact with the blood and an external face (72) which is in contact with the ambient air, the entire main closure element (68) being elastically deformable or displaceable along a deformation or displacement axis (A—A), which is substantially orthogonal to its general plane, under the effect of the blood pressure, the main closure element (68) being designed to engage with a load sensor (56) so that a portion of the external face (72) of the main closure element (68), in its rest state, is in direct or indirect contact with the load sensor (56) which can measure the force applied axially to the internal face (70) of the main closure element (68) by the blood pressure, in order to calculate therefrom the value of this pressure, characterized in that the pressure measurement section (46) comprises:

in its secondary wall (65), facing the hole (66) of the main wall (64), a secondary hole (84) which is sealed by a secondary closure element (86) having a deformation or displacement axis (A—A) which is substantially coincident with that of the main closure element (68), the area of the internal face (92) of the secondary closure element (86) being greater than the area of the internal face (70) of the main closure element (68), such that when the pressure of the blood is less than the pressure of the ambient air, the axial displacement of the secondary closure element (86) towards the main closure element (68) is greater than the axial displacement of the main closure element (68) towards the secondary closure element (86);

and comprising, in the compartment (58), a transmission spacer (94) which, when the pressure of the blood and the pressure of the ambient air are substantially equal, occupies a rest position in which the transmission spacer (94) is in contact by a first axial end (96) with the internal face (70) of the main closure element (68) and, by a second axial end (98), with the internal face (92) of the secondary closure element (86);

such that when the blood pressure is less than the ambient air pressure, the spacer (94) transmits the axial displacement, in the direction of the load sensor (56), from the secondary closure element (86) to the main closure element (68), so that the load sensor (56) can measure the resultant axial force in order to calculate therefrom the value of the blood pressure.

2. Device according to claim 1, characterized in that the pressure measurement section (46) comprises axial displacement guiding means (110, 112) for the transmission spacer (94).

3. Device according to claim 1, characterized in that the spacer (94) has an axial rod (100) provided, at least at one of its axial ends, with an axial support plate (96, 98), the external face (102, 104) of which is adjacent and substantially parallel to the internal face (70, 92) of the associated closure element (68, 86), when the spacer (94) occupies its rest position.

4. Device according to claim 3, characterized in that the rod (100) comprises a support plate (96, 98) at each one of its axial ends.

5. Device according to claim 3, characterized in that the area of the external face (102, 104) of each support plate (96, 98) is substantially equal to the area of the internal face (70, 92) of the associated closure element (68, 86).

6. Device according to claim 3, characterized in that each of the closure elements (68, 86) and each of the support plates (96, 98) has substantially the shape of a disc.

7. Device according to claim 3, characterized in that the internal face (106) of the main wall (64) and the internal face (108) of the secondary wall (65) each comprise a rim (110, 112), around the associated closure element (68, 86), which extends axially towards the inside and which delimits a section of guide tube of a diameter substantially equal to the diameter of the associated support plate (96, 98), for the purpose of axially guiding the transmission spacer (94).

8. Device according to claim 1, characterized in that the transmission spacer (94) is attached to one of the closure elements (68, 86).

9. Device according to claim 1, characterized in that at least one closure element (68, 86) is made in a single piece with the associated rigid wall (64, 65), and in that the transmission spacer (94) is made in a single piece with one of the closure elements (68, 86) which is made in a single piece with the associated rigid wall (64, 65).

10. Device according to claim 9, characterized in that the transmission spacer (94) is made by moulding with a closure element (86) which is itself made by moulding with the associated rigid wall (65).

11. Device according to claim 8, characterized in that the transmission spacer (94) is secured in axial displacement to the secondary closure element (86).

12. Device according to claim 1, characterized in that the area of the secondary closure element (86) is substantially twice the area of the main closure element (68).

13. Device according to claim 1, characterized in that the pressure measurement section (46) comprises a sensor which identifies the direction of the axial displacement of the secondary closure element (86), so as to determine whether the axial force measured by the load sensor (56) corresponds to a measurement of blood pressure which is above or below the pressure of the ambient air.

* * * * *